United States Patent
Davidson

(10) Patent No.: US 6,594,335 B2
(45) Date of Patent: Jul. 15, 2003

(54) X-RAY PHASE-CONTRAST MEDICAL MICRO-IMAGING METHODS

(76) Inventor: Charles J. Davidson, 1337 W. Farnum Ave., Royal Oak, MI (US) 48067

( * ) Notice: Subject to any disclaimer, the term of this patent is extended or adjusted under 35 U.S.C. 154(b) by 0 days.

(21) Appl. No.: 09/749,978

(22) Filed: Dec. 27, 2000

(65) Prior Publication Data

US 2001/0038680 A1 Nov. 8, 2001

Related U.S. Application Data

(60) Provisional application No. 60/173,238, filed on Dec. 28, 1999.

(51) Int. Cl.[7] ............................................. G21K 7/00
(52) U.S. Cl. ......................... 378/43; 378/119; 378/143
(58) Field of Search ............................ 378/43, 119, 143

(56) References Cited

U.S. PATENT DOCUMENTS 4,979,203 A * 12/1990 Radocaj ...................... 378/206
5,550,887 A * 8/1996 Schmal et al. ................ 378/43
5,606,588 A * 2/1997 Umstadter et al. .......... 378/119

* cited by examiner

Primary Examiner—Drew A. Dunn
Assistant Examiner—Jurie Yun

(57) ABSTRACT

These methods describe a collimated x-ray beam, used for in vivo phase-contrast x-ray imaging of the interior architecture of carbon-based objects, such as the intact human soft-tissue anatomy, for mapping the decrements of refraction experienced by the incident x-ray beam. These methods utilize a microscopically-thin laser-produced plasma x-ray spatial line-source, specified in the target plane as 50 microns or less in width and orthogonally, greater than one centimeter in length, requiring an optically-reflective mirror to line-focus cylindrically-shaped femtosecond pulses of infrared laser photons onto a heavy metal target. Bragg-diffractive multilayer x-ray mirrors collect a wide solid-angle of characteristic hard x-rays in the 15 KeV-to-100 KeV range from the spatial line-source, yielding a microscopically-thin x-ray fanbeam or x-ray slicebeam, specified in the object plane as 50 microns or less in width and orthogonally, greater than seven centimeters in length. These methods may employ slot-scanning and computed tomography for microscopic clinical x-ray imaging, such as for cancer-detection.

13 Claims, 2 Drawing Sheets

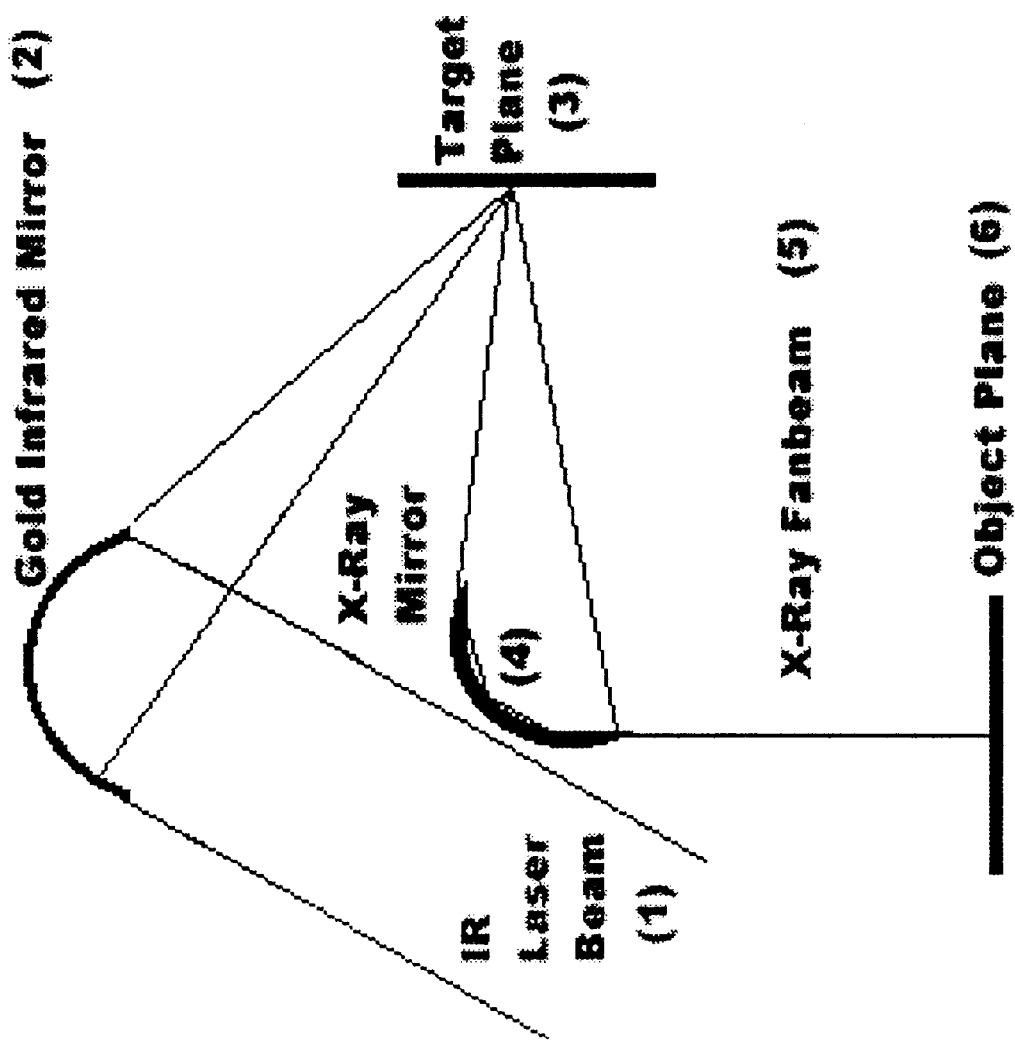

X-RAY PHASE-CONTRAST MEDICAL MICRO-IMAGING METHODS

REFERENCES

United States Patents Cited:

| | | | |
|---|---|---|---|
| 4,979,203 | Dec. 18, 1990 | Suckewer, et al. | X-ray laser microscope apparatus |
| 5,550,887 | Aug. 27, 1996 | Schmal, et al. | Phase contrast X-ray microscope |
| 5,606,588 | Feb. 25, 1997 | Umstadter, et al. | Method and apparatus for generating laser plasma x-rays |
| 5,850,425 | Dec. 15, 1998 | Wilkins | X-ray optics, especially for phase contrast |

Other References:

Murmane MM, Kapteyn HC, Rosen MD and Falcone RW. Ultrafast X-ray Pulses from Laser-Produced Plasmas. Science. 251: 531-536 (1991).

Krol A, Ikhlef A, Keiffer JC, Bassano DA et al. Laser-based microfocused x-ray source for mammography: Feasibility study. Medical Physics. 24(5): 725-32 (1997).

Chapman D, Thomlinson W, Johnston RE et al. Diffraction enhanced imaging. Phys. Med. Biol. 42: 2015-25 (1997).

Dilmanian FA, Zhomg Z, Ren B Wu XY, Chapman DL, Orion I and Thomlinson WC. Computed Tomography of x-ray index of refraction using the diffraction enhanced imaging system. Phys. Med. Biol. 45:933-946 (2000).

Kagoshima Y Tsusaka Y et al. Phase-Contrast X-Ray Imaging using Both Vertically and Horizontally Expanded Synchrotron radiation X-Rays with Asymmetric Bragg Reflection. Jpn. J. Appl. Phys. 38:1 480-472 (1999).

Arfelli F, Asante M et al. Low-dose phase contrast x-ray medical imaging. Phys. Med. Biol. 43: 2845-52 (1998).

Pisano ED, Johnston RE, Chapman D et al. Human breast cancer specimens: diffraction-enhanced imaging with histologic correlation -- improved conspicuity of lesion detail compared with digital radiography. Radiology 2000 Mar; 214(3):895-901.

Mamose A et al. Tomographic image reconstruction using x-ray phase information. SPIE. 2708: 674-684 (1996).

Ingal VN and Baliaevskaya EA. X-ray plane-wave topography—observation of the phase contrast from a non-crystalline object. J. Phys. D 28: 2314-17 (1995).

Gao D, Pogany A, Stevenson AW and Wilkins SW. Phase-Contrast Radiography. Radiographics.18:1257-67 (1998).

Snigiriev A, Snigireva I, Kohn V, Kuznetsov S and Schelokov I. On the possibilities of x-ray phase contrast microimaging by coherent high-energy synchrotron radiation. Rev. Sci Instrum. 66(12): 5486-92 (1995).

Kotre CJ and Birch IP. Phase contrast enhancement of x-ray mammography: a design study. Phys. Med. Biol. 44: 2853-2866. (1999).

Fitgerald R. Phase-Sensitive X-Ray Imaging. Physics Today Online. (2000).

Golovchenko JA and Liu C. X-Rays in Curved Spaces. *X-Ray and Inner Shell Processes: 18th International Conference. American Institute of Physics Conference Proceedings.* pp. 621–637. (1999).

Brauer S, Stephenson GB et al. Asymmetrically cut crystals as optical elements for highly collimated x-ray beams. Rev. Sci. Inst. 66(2): 1506-1509 (1995).

FIELD OF THE INVENTION

This invention relates to systems and methods for creating a beam of penetrating radiation, that is to be deflected within an object, to image the internal structure of the object, in particular, of biological soft-tissues and other materials that are not significantly absorbing to x-rays.

BACKGROUND OF THE INVENTION

X-rays are widely used to study the internal structure of various objects. X-ray imaging is a subject of great international interest because of its capacity for high penetrability into animal soft-tissues, which is related to the short wavelength of x-rays.

Conventional radiographic imaging methods, are based upon the difference between photoelectric absorption of x-rays between soft-tissue and bones or contrast media. Unfortunately, at high energies utilized to image deep body tumors, the image contrast of soft-tissues due to absorption decreases markedly. This is because low-Z elements, such as carbon-based biological soft-tissue with an average atomic number of Z equal to 7.64, do not appreciably absorb high energy medical x-rays (which are between 15 KeV and 100KeV). Soft-tissue are mostly transparent to these hard x-ray photons. The calcium in bones has a much higher Z-value of 20, iodine in contrast media has a Z-value of 53.

Soft-tissue imaging is perhaps the most vexing problem in clinical radiography, while magnetic resonance imaging of soft-tissues has inadequate resolution for this purpose in many cases. Some "partial-exceptions" to soft-tissue x-ray imaging limitations exist, but they are profoundly limited in there clinical utility. For example, in x-ray computed tomography, one may delineate some soft-tissue contrast, from the summation of many views of very small differences in x-ray absorption, provided that the detail is not too small. Mammography is another partial-exception to soft-tissue x-ray imaging limitations. With mammography, photoelectric absorption of molybdenum k-alpha x-rays by glandular soft-tissues of the breast is sometimes able to transfer low amounts of contrast from larger tumors, provided that the breast tissue is not very thick. Mammography can detect submillimeter "microcalcifications" that may indicate cancer, however, several common benign conditions may also produce microcalcifications. And mammography still does not delineate tumor architecture, such as margins, invasiveness, small metastasis, or a microscopically-detailed vascular signature, with capillaries ranging in size from 8-to-20 microns in diameter.

Statistically, mammography currently has a very high rate of false positives and false negatives. In a population of undiagnosed women advised by their doctors to have regular diagnostic screening, only five women out of 1000 will actually have breast cancer. But for that same population, the rate of positive mammograms will be 10%--the ratio of false positives to true negatives is nearly 20:1. And for about 10–20% of women who have palpable abnormalities, the mammograms won't show anything. There is thus a driving need to improve breast cancer detection technology. (Fitzgerald)

Compared to x-ray absorption imaging, phase-contrast imaging is better suited for delineating soft-tissue structures that do not appreciably absorb x-rays, but that may contain many non-absorptive structural details with diameters between one micron and one millimeter. Phase-contrast imaging is any technique that renders variations in the refractive index of a non-absorbing object visible. A phase-shift of x-ray photons is characterized by slight deviations from their incident path as they traverse through an object, such as animal soft-tissues, which occurs after the photons interact briefly and elastically with the atoms in their path. A phase-shift is a type of deflection of the incident beam within a material that is typically in the range of one-to-ten microradians. The phase-shift, when adequately large, shifts the intensity of the deflected ray to a different place on a detector, such as an adjacent pixel (in the x- or y-direction).

Coherent light, a requirement for phase-contrast imaging may be represented as a bundle of rays that are each parallel to the optical axis. A coherent beam of light may be produced by lasers at visible, UV or IR frequencies, but presently, only by using synchrotron undulators can a coherent beam of "light" be produced with hard x-rays. The x-ray phase-shifts experienced by an incident beam can be observed as a microradian deflection only when employing a coherent beam of incident light, with no transverse beam divergence, to illuminate the object under investigation.

Coherent light may also be represented as a train of unperturbed planar wavefronts, that are aligned parallel to the detector plane and that propagate along the optical axis. After a homogenous, planar incident wavefront interacts with the constituent low atomic number atoms of the specimen, a wrinkle (i.e., a warping) is produced in the formerly perfect planar wavefront, because of refractory effects. In other words, spatial three-dimensional distortions may be impressed upon the planar incident wavefront by specific density-dependent and chemical-dependent biological soft-tissue interfaces within the illuminated object. Thus, the incident plane-waves are converted in the object into a three-dimensionally distorted and indented wavefront, which possesses a phase-shifted profile, capable of producing areas of non-homogenous intensity upon a two-dimensional detector.

Importantly, refractory disturbances are maximal at interfaces of different refractory surfaces within the object that are oriented parallel to the incident beam direction. Therefore, since phase-contrast is greatest at the edges of internal soft-tissue structures that are oriented parallel to the optical axis, x-ray phase-contrast imaging is an edge-enhanced imaging method.

The phase-shifts experienced by an incident beam cannot, however, be observed using a standard conventional x-ray tube that has primarily spatially non-coherent x-rays, due to large amounts of cross-over x-rays that emanate from relatively distant locations within the large macroscopic focal-spot, that has a visible diameter ranging from 0.3-to-2.0 millimeters. Thus, a standard clinical x-ray tube cannot be used effectively for phase-contrast imaging.

Thick cancerous human tissues have been observed as internally distinct in structure from normal tissues. Cancerous tissues appear to have a chaotically disordered microscopic structure, compared to non-cancerous adjacent soft-tissues. X-ray phase-contrast imaging is ideally suited for the detection of cancerous tissues when they are still microscopic and are possibly at an earlier stage of carcinogenic development than a larger mass and when they are thus, more treatable.

It has been noted that for low energy 1.24 KeV nonmedical "soft" x-rays, a microscopic carbon fiber of approximately 3 microns in diameter produces a full 2pi phase-shift and 50% absorption, which are both adequate values for their respective imaging methods. However, for high energy 12.4 KeV x-rays, a much larger 3 millimeters diameter carbon fiber is required to produce 50% absorption, while only 30 microns can still produce a full 2pi phase-shift (Snigiriev et al). In contarst to x-ray absorption imaging, with phase-contrast mammography using synchrotron-produced "hard" x-rays, equivalent images of phantoms were obtained at 30 keV, at a twenty-fold reduction in dose, compared to phase-contrast images taken at 17.5 keV, representing the normal mammographic x-rays at the molybdenum k-alpha emission peak. (Pisano et al). Thus, only by using both the harder coherent medical x-rays and phase-contrast imaging techniques, can one detect microscopic detail in thick, non-absorbing objects at lower doses (because of the use of higher energy x-rays that are more tissue-penetrating).

In general, there are three basically different types of x-ray phase-contrast imaging techniques, involving either: 1) holographic interferometry, 2) placing an analyzer crystal after the object, or 3) using direct in-line geometry, without a crystal analyzer, producing either an analog image or employing a mathematical processing of intensity information (that impinges upon a digital-detector).

In the x-ray phase-contrast imaging technique using a Bragg-diffractive analyzer crystal that is placed after the object, the analyzer surface is geometrically aligned within the incident beam, to be more-or-less parallel to the incident beam. Because of this specific analyzer-beam geometry and also because of the crystal's uniformly oriented diffraction planes, the analyzer crystal possesses a rocking curve which is sensitive to the microradian alterations in the direction of the incident beam, that are induced by changes in the refractive index within soft-tissues. Thus, depending on the orienation of the crystal to the incident beam of coherent x-rays, the analyzer crystal can select for either the phase-contrast image (from the deflected beam) or the absorption-contrast image (from the direct beam). Furthermore, in both cases of absorption and of refraction, the analyzer crystal is used simultaneously as a Compton scatter reduction optic (Ingal et al, Chapman et al). Using diffraction enhanced imaging (DEI) the two images from the opposite sides of the rocking curve are then combined on a pixel-by-pixel basis to obtain a single image that contains both refraction and absorption information.

In quantitative phase-contrast imaging systems employing high brightness synchrotron radiation, rapid, low dose and high resolution images were acquired of both mammographic phantoms and thick cancerous human breast tissue (Arfelli et al, Pisano et al). Only by using coherent x-rays can the simplified version of the Fresnel-Kirchhoff Integral can be used to mathematically reconstruct the phase-image, on a pixel-by-pixel basis, from measurements of intensity variations at the detector.

Three requirements are necessary for constructing a clinical phase-contrast imaging system; adequate collimation, adequate flux and hard x-rays. First, both image resolution and collimation of an incident x-ray beam are inversely proportional to the size of the source. As represented by the MTF curve in Kroll et al, the absorption contrast for a typical mammographic focal-spot (of 500 microns in diameter) was nearly undetectable for the same size spatial frequency, namely at 40 line pairs per millimeter, where remarkably, the absorption contrast remained nearly undiminished from a microscopic size laser-produced x-ray source (of 48 microns in diameter).

Second, it should be noted that a pinhole-collimated, microscopic point source x-ray tube can only produce a low-power microbeam, since the flux is limited to 0.75 watts per micron in focal-spot diameter. Phase-contrast images of soft-tissues have been produced using low power circular microfocus x-ray tubes, but the organ samples were required to be thin and the durations of image aquisition were far to long for clinical applications (Gao et al). Thus, a small size x-ray source, while producing a more spatially coherent beam, produces inadequate x-ray flux for clinical imaging. A high flux beam is required for clinical imaging, that must be rapid, to prevent motion blur and must have a higher signal-to-noise ratio than a more slowly acquired image.

Third, the x-rays must be hard x-rays, in the 17 KeV-to-100KeV, range for use in clinical x-ray imaging of an entire view of the whole aspects of human anatomy, without biopsy.

For clinical phase-contrast x-ray imaging requirements, one needs a high-flux hard x-ray source, specified as a highly elongated x-ray line-source, microscopically-thin, but greater than a centimeter long, in the target plane. Such a high-flux x-ray line-source has a much larger total cross-sectional area than a low-flux pinhole-collimated point-source. The term "microscopic" can be described as 50 microns or less across.

Using a highly-elongated x-ray line-source, one may produce a high-flux and ultrathin x-ray fanbeam or slicebeam, that is spatially-coherent, specified as microscopically-thin in only one direction in the object plane, but greater than 7 centimeters long. Multilayer x-ray mirrors, aligned in the optical axis and satisfing the Bragg condition for hard x-rays, can be used to control both the thinness and lateral length of the fanbeam and slicebeam in the object plane. Such a microscopically-thin hard x-ray fanbeam or slicebeam can be used to produce clinical phase-contrast x-ray images, having microscopic resolution, by slot-scanning and computed tomography methods.

The phase-contrast patent of Schmal et al specifies the use of a micro-zone plate, with the narrowest d-spacings of several nanometers, as a focusing device. Microzone plates can only be used for soft x-rays that are less than 10 keV energy, corresponding to 1.24 nanometers wavelength. The Suckewer patent, also with a microzone plate mentions potential biological imaging at the water window specifically between 2.9 and 4.4 nanometers. Neither of these two patents specifies a manner of obtaining sufficient energy photons with sufficiently short wavelengths, capable of penetrating a thick intact human anatomy. Most soft-x-rays are absorbed within a few millimeters under the surface in carbon-based soft-tissues.

Hard x-ray-diffractive optics satisfying the Bragg-condition already exist, such as bent, asymmetrically-cut crystalline silicon or curved pyroltic graphite or confocal graded-multilayer x-ray mirrors that are made from alternating high-atomic number and low-atomic number materials, such as WB4C. In contrast to a circular manufactured micro zone-plate used in those patents, with d-spacings in the order of at least several nanometers, silicon, because it has a much smaller d-spacing than those of micro-zone plates, about 0.54 nanometers, can diffract harder, shorter wavelength x-rays.

The use of the Suckewer et al invention to detect early cancer cells (with soft x-rays) must, therefore, also be performed ex-vivo, that is, as a specimen already removed from the human body. Such a device as specified by Suckewer cannot be used for public health clinical x-ray screening, for example, as with mammography.

Previously, a laser-produced collisional x-ray source could not generate the necessary amounts of coherent x-ray flux that are needed to rapidly acquire, in a clinically-appropriate time interval, a phase-contrast image of the internal structure of an object as thick as the human anatomy, such as, a human torso or the head and neck. A microscopic dimension of a small circular point-like x-ray source is described in the patent of Umstadter et al. A version of the microfocus x-ray tube from the Wilkins patent has a microscopically-thin line-source that is perpendicular to the plane of diffraction of the x-ray mirrors. The Wilkins invention comprises an electron collision with the target, having a minimum focal-spot size that is limited by electrostatic repulsion, about 20 microns.

In contrast to the patent of Umstadter et al, vastly greater amounts of coherent x-ray flux, sufficient for clinical phase-contrast imaging, could be obtained by extending the microscopically-narrow line-source in only one direction in the target plane. That lateral-only extension in the target plane greatly increases the spatial surface area of the plasma and thus, the overall x-ray flux. A spatial x-ray line-source is not described in the patent of Umstadter et al for the production of a high-flux and spatially-coherent x-ray fanbeam or x-ray slicebeam.

SUMMARY OF THE INVENTION

An object of the invention is to provide an x-ray line-source in which a laser-generated x-ray source has a controlled source length that is substantially greater than a controlled source width.

The methods of the present invention describe a collimated x-ray beam, that can be used for phase-contrast x-ray imaging of the interiors of carbon-based objects, that are minimally absorbing to x-rays, such as the intact human soft-tissue anatomy, for mapping the decrements of refraction experienced by the incident x-ray beam.

These methods comprise clinical phase-contrast x-ray imaging, with microscopic resolution, defined as visualizing an internal structure 50 microns across or less, using a microscopically-thin x-ray fanbeam or x-ray slicebeam for slot-scanning and computed tomographic imaging.

First, these methods uitilize a highly elongated laser-produced plasma x-ray line-source, with only one microscopic dimension in the target plane, specified as 50 microns or less in width and greater than one centimeter in length, in the target plane. These methods require an optically-reflective mirror, such as made from highly-polished gold, to line-focus a femtosecond pulse of infrared laser photons for collision onto a molybdenum or higher atomic number metal target, such as tungsten. The present invention comprises a line-focused laserbeam, having a focal-spot size that is not limited to electrostatic repulsion, with a limit as small as the infrared wavelength produced by the laser, about one micron.

Second, Bragg-diffractive x-ray mirrors collect a wide solid-angle of hard x-rays in the 15K-to-100 KeV range from the line-source, yielding a microscopically-thin x-ray fanbeam or x-ray slicebeam that has only one elongated dimension in the object plane, specified as 50 microns or less in width and greater than 7 centimeter in length, perpendicular to the optical axis.

Hard x-ray mirrors are Bragg-diffractive optics, such as bent, asymmetrically-cut crystalline silicon or curved pyroltic graphite or confocal graded-multilayer x-ray mirrors made from WB4C, an alternating high-atomic number and low-atomic number layered material. In contrast to a circular manufactured microzone-plate used in the Schmal et al and Suckewer et al patents, with d-spacings in the order of at least several nanometers, silicon can diffract harder, shorter wavelength x-rays because it has a much smaller d-spacing by an order of magnitude, about 5.4 Angstroms. The flux-capturing efficiency of the multilayer x-ray mirror is significantly increased when it's d-spacings are aligned parallel to the long-axis of the x-ray line-source, justifying the use of bent asymmetrically-cut silicon as a Bragg-diffractive x-ray focusing-optic, by virtue of silicon's having an orthogonally- oriented diamond-shaped crystal lattice.

The incident beam in the object plane is described as a monochomatic or quasimonochomatic x-ray fanbeam or x-ray slicebeam, that is collimated, with a spatial divergence away from the optical axis of preferentially less than 10 microradians. A microscopically-thin x-ray fanbeam or x-ray slicebeam is not described in Umstadter et al.

The x-ray fanbeam or x-ray slicebeam of the present invention can also be used for producing an x-ray absorption image with microscopic resolution, that is absent of Compton-x-ray scattering effects.

DETAILED DESCRIPTION OF THE INVENTION

Figure 2:
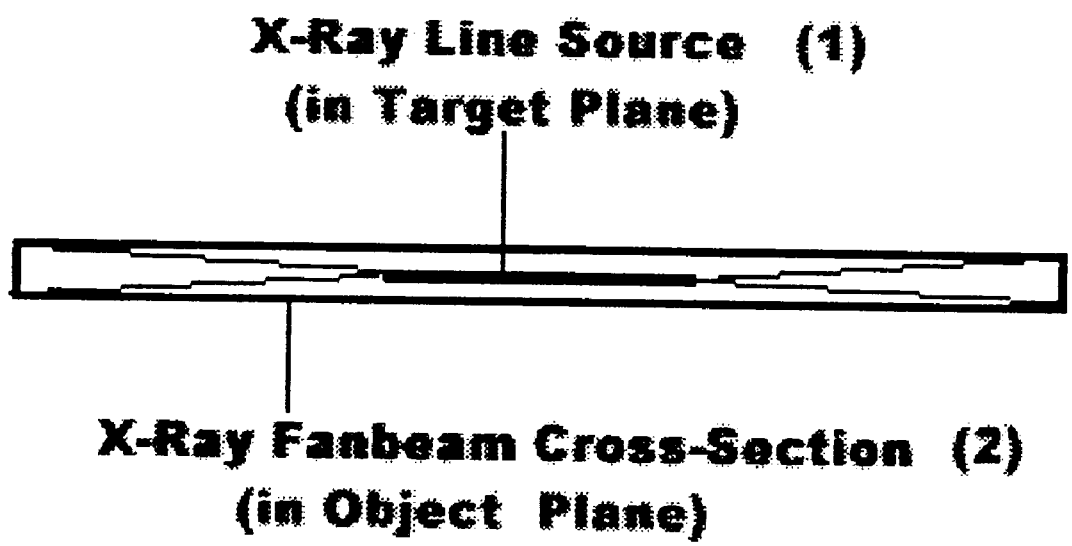
FIG. 2 is a schematic representation of the x-ray fanbeam (2) viewed along the optical axis from the vantage point of the plane of the object and the more distant x-ray spatial line-source (1) that should be recognized as.being positioned in the background, in the target plane. Both the x-ray line source and the x-ray fanbeam are equally centered relative to the optical axis and both entities are described as having a microscopic dimension in their vertical, width direction only. It should be noted that the length-to-width aspect ratio of both the x-ray spatial line-source and the x-ray fanbeam cross-section are greatly reduced from claims 1 and 2 of this patent, in order to aid in the schematic visualization of the system. It should also be noted that the long-axis of the x-ray line-source is parallel to the long axis of the highly elongated rectangular wavefront of the x-ray fanbeam. Both entities, (1) and (2), represented in FIG. 2 are mutually parallel to the Bragg-diffracting planes of the intervening x-ray mirror, although the representation of the x-ray mirror has not been included in the diagram.
Figure 1:
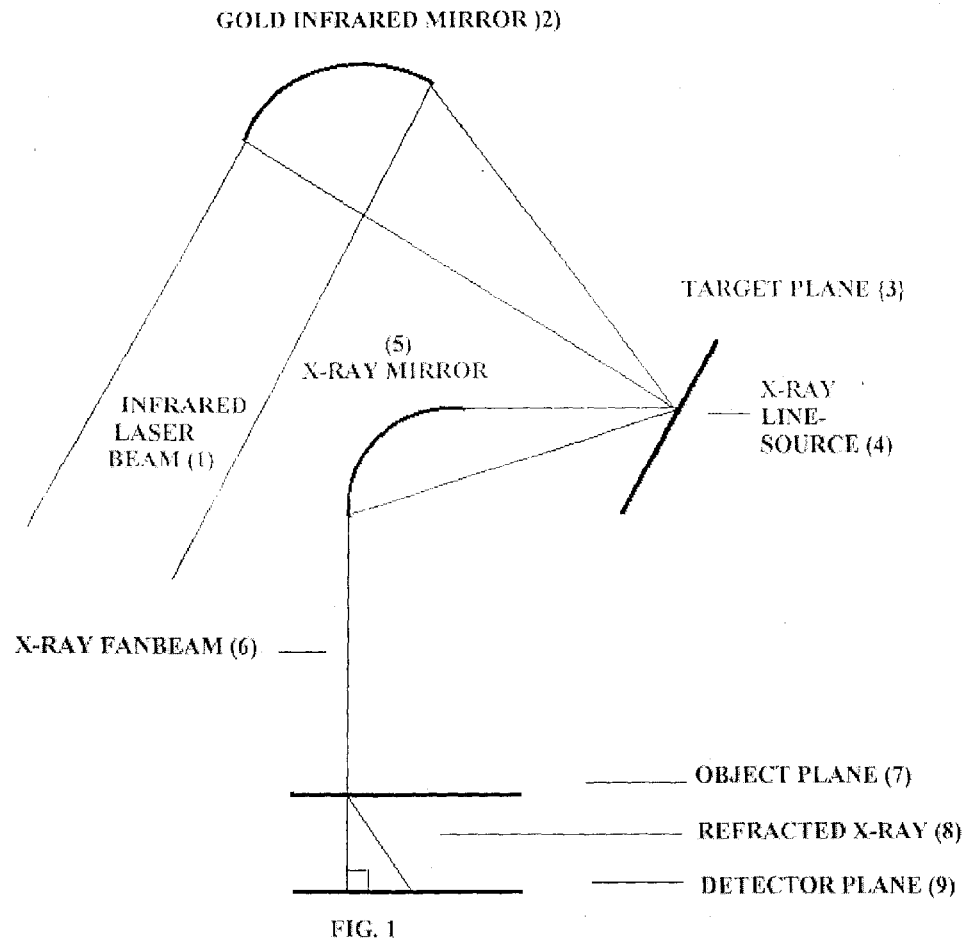
FIG. 1 is the side-view of a schematic representation of a system for generating a microscopically-thin x-ray fanbeam (6) from a laser-produced plasma x-ray (spatial) line-source (4) that is microscopically-thin in the plane of the target (3). The scheme illustrated in FIG. 1 depicts a single x-ray-reflective Bragg-diffracting x-ray mirror (5), that focuses a solid-angle of x-rays from the x-ray spatial line-source (4), to create the microscopically-thin x-ray fanbeam (6). Although the laser itself is not depicted in this schematic representation, the infrared laser beam (1) is depicted as being reflected off of an infrared-reflective, highly polished gold mirror (2) that has a spatially extended line-focus (4) upon the heavy metal target (3). Note that both the infrared line-focus (4)) and the x-ray fanbeam (6) are observed as microscopic when viewed from the side. The detector plane (9) is depicted as intersecting the refracted x-ray (8) that was refracted from within the object plane (7).
Figure 2:
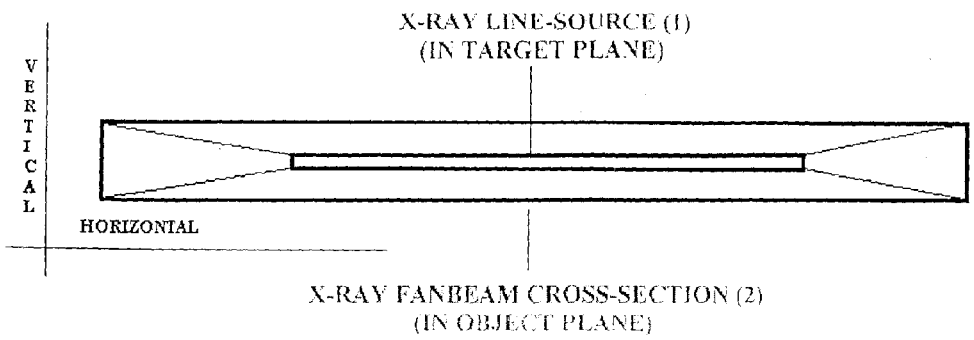

An object of the invention is to provide an x-ray line-source in which a laser-generated x-ray source has a controlled source length that is substantially greater than a controlled source width.

The methods of the present invention describe a collimated x-ray beam, that can be used for phase-contrast x-ray imaging of the interiors of carbon-based objects, that are minimally absorbing to x-rays, for mapping the decrements of refraction experienced by the incident x-ray beam.

These methods are for non-invasively observing the contrast-inducing refractive effects of microscopic carbon-based structures, that are minimally x-ray-absorbing and located internally within much larger intact carbon-based objects, where the term "microscopic", defines an internal structure 50 microns across, or less.

These methods comprise clinical phase-contrast x-ray imaging, with microscopic resolution, using a microscopically-thin x-ray fanbeam or x-ray slicebeam for slot- scanning and computed tomographic imaging.

These methods describe noninvasive in-vivo imaging the interiors of much larger intact objects, for example of the size, density and composition of the various entire aspects of human soft-tissue anatomy, without biopsy or of industrial materials, such as lumber, nondestructively.

These methods are capable of detecting various noncarbon-based entities, such as microcalcifications within cancerous tissues, imaged in vivo within a clinical setting and microscopic voids, such as alvioli of the lungs or hairline cracks in industrial materials.

First, these methods utilize a highly elongated laser-produced plasma x-ray line- source, with only one microscopic dimension in the target plane, specified as 50 microns or less in width and greater than one centimeter in length, in the target plane. These methods require an optically-reflective mirror, such as made from highly-polished gold, to line-focus a femtosecond pulse of infrared laser photons for collision onto a molybdenum or higher atomic number metal target, such as tungsten. The present invention comprises a line-focused laser, having a focal-spot size that is not limited to electrostatic repulsion, with a limit as small as the infrared wavelength produced by the laser, about one micron.

Second, Bragg-diffractive x-ray mirrors collect a wide solid-angle of hard x-rays in the 15K-to-100 KeV range from the line-source, yielding a microscopically-thin x-ray fanbeam or x-ray slicebeam that has only one elongated dimension in the object plane, specified as 50 microns or less in width and greater than 7 centimeter in length, perpendicular to the optical axis.

Hard x-ray mirrors are Bragg-diffractive optics, such as bent, asymmetrically-cut crystalline silicon or curved pyroltic graphite or confocal graded-multilayer x-ray mirrors made from WB4C, an alternating high-atomic number and low-atomic number layered material. In contrast to a circular manufactured microzone-plate used in the Schmal et al and Suckewer et al patents, with d-spacings in the order of at least several nanometers, silicon can diffract harder, shorter wavelength x-rays because it has a much smaller d-spacing by an order of magnitude, about 5.4 Angstroms. The flux-capturing efficiency of the multilayer x-ray mirror is significantly increased when it's d-spacings are aligned parallel to the long-axis of the x-ray line-source, justifying the use of bent asymmetrically-cut silicon as a Bragg-diffractive x-ray focusing-optic, by virtue of silicon's having an orthogonally-oriented diamond-shaped crystal lattice.

These methods describe an x-ray transmissive Bragg-diffractive focusing-optic to diffract the x-ray beam laterally in order to produce a incident wavefront that is at least seven centimeters long in the object plane, while still maintaing a microscopic beam thickness. Examples specifying allowable x-ray transmissive focusing materials include, bent, asymmetrically-cut crystalline silicon placed in the Laue configuration, that is preferential, or a metal-cladded glass polymicrocapillary lens, or a curved leaded glass microchannel plate.

The incident beam in the object plane is described as a monochomatic or quasimonochomatic x-ray fanbeam or x-ray slicebeam, having a 10 percent or less spread in energy bandwidth for 95 percent or more of the x-ray photons diffracted.

Central to the methods of the present invention, the incident beam in the object plane is described as collimated, with a spatial divergence away from the optical axis of preferentially less than 10 microradians. In addition, a microscopically-thin x-ray fanbeam or x-ray slicebeam is not described in Umstadter et al.

Both in the target plane and in the object plane, that may be non-parallel to each other, the present invention may arbitrarily be described as having horizontal and vertical directions, with respective length and width dimensions. The horizontal dimension, in the target plane, specifies the long-axis of the x-ray line-source. And in the object plane, the horizontal dimension specifies the long-axis of the resultant x-ray fanbeam or x-ray slicebeam, that have highly elongated rectangular beam cross-sections. Moreover, the long-axis of the x-ray line-source is distinctly parallel to the long axis of the elongated x-ray beam wavefront and both entities are equally centered relative to the optical axis.

Significantly, in the present invention, the vertical dimension is microscopic for the x-ray line-source in the target plane. The vertical dimension is also microscopic, in the object plane, for the cross-section of the the x-ray fanbeam and x-ray slicebeam. The use of the microscopically-thin, yet highly extended, plasma x-ray spatial line- source contributes—in the vertical, width direction—to the resultant x-ray fanbeam or x-ray slicebeam having an adequate degree of collimation for their use in phase-contrast x-ray imaging.

The spatial measure of the degree of collimation of a beam—that is, how closely the rays of a beam approach being parallel to the optical axis, with a minimal amount of beam divergence away from the optical axis—is mathematically defined as the lateral coherence length, "D", over which phase relations are preserved. The lateral coherence length, which is given in Kotre and Birch by the inverse mathematical relation, relative to the focal spot size;

$$D=[lambda*r(1)]/f$$

where lambda is the wavelegth, r(1) is the source-to-object distance and f is the size of the focal spot. Thus, if the x-ray line-source is specified as microscopic in only one direction in the plane of the target, it can be said to have an extremely small value for its width, "f", in the vertical direction. Importantly, from the inverse relation stated above, with a small value of "f", the measure of x-ray beam collimation, the lateral coherence length, "D", increases.

Moreover, the use of multilayer diffractive x-ray mirrors described in claim 20 of the present invention to create a microscopically-thin x-ray fanbeam or x-ray slicebeam, also contributes towards the increased value of lateral coherence, by having rays that more closely approach being parallel to the optical axis. This follows from Braggs Law for x-ray diffraction;

$$lambda=2d*sin(theta),$$

where lambda is the wavelength, d is the spacing between the diffracting atomic planes and theta is both the x-ray incident/acceptance angle and the diffraction angle, that are equal relative to their bisecting vector that is normal to the diffracting atomic planes. Those divergent x-rays that fall outside of the allowable acceptance angle of the x-ray mirror are excluded, both vertically and horizontally, from being diffracted towards the object, since the Bragg condition is not satisfied for those excluded x-rays.

Therefore, by using both a microscopically-thin x-ray line-source and x-ray mirrors for beam collimation, the resultant x-ray fanbeam and x-ray slicebeam have adequate values of lateral coherence for their use in x-ray phase-contrast imaging, specified in claim 2 as having a beam divergence of less than 100 microradians, although less than 10 microradians is preferable.

Using a commercially-available low flux microfocus x-ray tube, only 0.75 watts of x-rays are produced per micron of diameter in the circular x-ray focal spot. Alternatively, a high flux x-ray fanbeam or x-ray slicebeam can be produced by the extreme horizontal elongation of the microscopically-thin x-ray line-source to a length that is greater than one centimeter, thereby having a length-to-width aspect ratio of at least 200. This extreme elongation of the x-ray line-source, in one direction only, results in a proportionate linear increase in both the cross-sectional beam area and in the beam's corresponding x-ray flux. Also, Bragg-diffractive x-ray mirrors are used for additional beam collimation purposes, that are capable of capturing a particularly wide solid-angle of x-rays. The use of x-ray mirrors allows for the generation of a much higher flux x-ray fanbeam or x-ray slicebeam, compared to slit collimation methods where a significant amount of x-rays are excluded. Therefore, the high flux of x-rays that are available in the collimated x- ray beam of the present invention may be used for clinical phase-contrast x-ray imaging, for visualizing in-vivo, the microscopic detail within intact human soft-tissue anatomy.

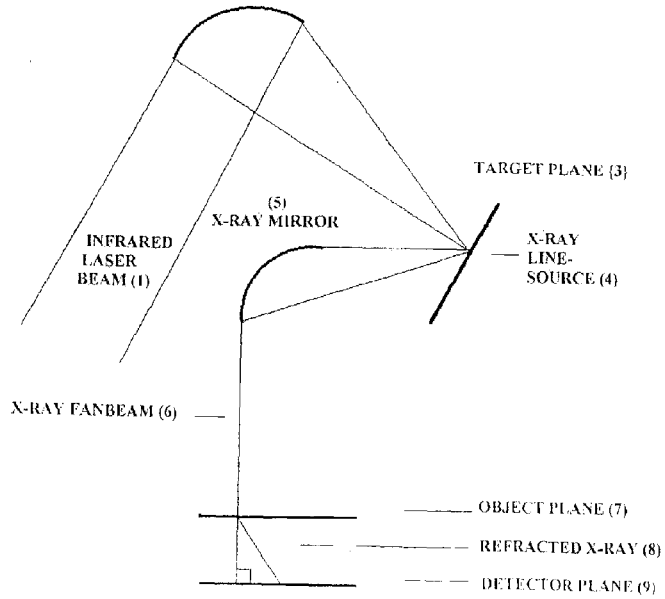

I claim:

1. The method for creating an in vivo x-ray image of the interior of an illuminated object, where the illuminated object induces x-ray absorption and/or detectable x-ray refraction, an induced deviation in the direction of the incident x-ray beam;

wherein the in vivo x-ray imaging method utilizes an illuminating x-ray source, that is a microscopically-thin x-ray line-source comprising a laser-produced plasma generated by optically focusing a high power femtosecond-pulsed terawatt laserbeam, onto a molybdenum or higher atomic number metal target;

where, in the plane of the target, the plasma x-ray spatial line-source dimension, microscopic in width only, is 50 microns across or less in only one direction in the plane of the target;

further, where in the plane of the target, the plasma x-ray spatial line-source length dimension, in the direction perpendicular to the microscopic width direction, is greater than one centimeter long;

the spatial x-ray line-source width is specified as vertical in the plane of the target and the spatial x-ray line-source length is specified as horizontal in the plane of the target;

using laser-produced photons in the visible or infrared wavelengths that are reflected off of an off-axis aspherical mirror or dual mirror assembly and optically line-focused into a microscopically-thin collision upon the molybdenum or higher atomic number metal target; yielding plasma-generated hard x-rays in the 15 KeV-to-100 KeV range;

using either a single mirror or a dual mirror assembly that has an off-axis parabolic primary reflective surface followed by a cylindrical reflective surface, for focusing a visible wavelength or infrared cylindrically-shaped laser beam having an initial circular cross-section into a spatial line-focus upon the target.

2. The method for utilizing x-ray mirrors for the focusing of laser-produced x-rays that emanate from the x-ray spatial line-source of claim 1 to produce an x-ray slicebeam or x-ray fanbeam having a highly elongated rectangular wavefront profile, that is microscopically-thin in only one direction in the plane of the object, perpendicular to the optical axis;

where, in the planes of the object, perpendicular to the microscopically-thin width direction, the elongated x-ray wavefront profile is at least seven centimeters long;

the microscopic x-ray wavefront cross-sectional width dimension is specified as vertically-directed in the plane of the object and the wavefront cross-sectional length is specified as horizontally-directed in the plane of the object;

where, located between the source and the object, are one or two successive Bragg- diffractive x-ray mirror optics, x-ray reflective devices aligned within the optical axis that are designed for focusing 15 KeV to 100 KeV hard x-rays when the Bragg condition is satisfied;

where the long-axis of the x-ray line-source is parallel to the planes of diffraction of the x-ray mirrors;

whereby a solid angle of the semicylindical wavefront that emanates from the x-ray line-source is intercepted by x-ray mirrors to produce a microscopically-thin and high brightness x-ray fanbeam or x-ray slicebeam, collimated in the direction away from the optical axis to less than 100 microradians;

the long-axis of the x-ray line-source is parallel to the long axis of the highly elongated rectangular wavefront of the x-ray fanbeam or x-ray slicebeam, by virtue of both entities being mutually parallel to the Bragg diffracting planes of the x-ray mirrors;

using x-ray mirrors for the spectral conditioning of a broad spectrum of plasma- produced x-rays in order to create an x-ray fanbeam or x-ray slicebeam that is in the 15 KeV-to-100 KeV energy range and that is either nearly monochromatic or quasi-monochromatic having a 10 percent or less spread in energy bandwidth for 95 percent or more of the x-ray photons diffracted.

3. The method of 20 for illuminating an object with x-rays, in the 15 KeV-to-100 KeV range, with a microscopically-thin and collimated x-ray fanbeam or x-ray slicebeam to yield an in vivo phase-contast x-ray image of an object;

that non-invasively maps the decrements of refraction experienced by the collimated incident x-rays in an object's interior and is capable of microscopic resolution, absent the effects of Compton scattered x-rays;

non-invasively observing the contrast-inducing refractive effects of microscopic carbon-based structures, that are located internally within much larger intact carbon-based objects;

noninvasive in-vivo imaging the interiors of much larger intact objects;

and of detecting various noncarbon-based entities, imaged in vivo.

4. The method of claim 3 for non-invasively creating an in vivo phase-contrast x-ray image of a human subject, in the form of clinical radiography;

of subject illumination by slot-scanning techniques, utilizing a microscopically-thin x-ray fanbeam or x-ray slicebeam to yield phase-contrast x-ray images;

for the non-invasive delineation of refraction-inducing microscopic soft-tissue architecture.

5. The method of claim 3 for in vivo phase-contrast x-ray imaging for the detection of malignancies in a human subject, wherein said malignant microscopic structures are 50 microns or less in size;

creating an in vivo phase-contrast x-ray image for the early detection of cancer in living persons, non-invasively and without the use of a biopsied specimen;

for the detection of very small metastasis that are smaller than three millimeters across, invasive tumor margins and tumor-associated microcalcifications.

6. The method of claim 3 for the non-destructive phase-contrast x-ray imaging of the interiors of carbon-based industrial materials, utilizing an x-ray fanbeam or x-ray slicebeam that has only one microscopic dimension in the planes of the object;

high throughput phase-contrast x-ray imaging for purposes of monitoring fluidic turbulence within pipelines and for assessing the turbulence within plasmas and jets.

7. The method of claim 3 for in vivo phase-contrast computed tomographic x-ray imaging of the interior of a human subject, with microscopic resolution, utilizing an x-ray fanbeam or x-ray slicebeam beam that has only one cmicroscopic dimension in the planes of the object.

8. The methods described in claim 2 for producing an in vivo x-ray absorption image of the interior of an intact object, that is primarily composed of carbon-based molecules, but not limited to such composition, utilizing monochromatic x-rays, or quasimonochromatic x-rays, in the energy range of 15 KeV-to-100 KeV;

for object illumination purposes, that utilizes a microscopically-thin laser-produced plasma x-ray line-source, that has only one microscopic dimension in the plane of the target;

that utilizes x-ray mirrors to produce a collimated x-ray fanbeam or x-ray slicebeam, that is microscopically-thin in only one direction in the planes of the object.

9. The method of claim 8 for the non-destructive testing by x- ray absorption imaging techniques of low atomic number carbon-based industrial materials that can be greater than three millimeters in thickness;

utilizing a microscopically-thin x-ray fanbeam or x-ray slicebeam for the high throughput, non-destructive x-ray absorption imaging of industrial materials, with microscopic resolution.

10. The method of claim 8 for in vivo clinical x-ray absorption radiography, of a human subject, that is capable of microscopic resolution and rejects Compton scattered x-rays;

subject illumination by slot-scanning that utilizes an x-ray fanbeam or x-ray slicebeam, that is microscopically-thin in only one direction in the planes of the object.

11. The method of claim 8 for computed tomographic x-ray absorption imaging that utilizes a microscopically-thin x-ray fanbeam or x-ray slicebeam for object illumination, being clinically capable of microscopic resolution with a human subject, that rejects Compton scattered x-rays.

12. The method of claim 2 further using an x-ray transmissive Bragg- diffractive Laue focusing-optic to diffract the x-ray beam laterally, in the horizontal direction, in order to produce an x-ray fanbeam or x-ray slicebeam having a wavefront that is at least seven centimeters long in the object plane, while still maintaining a microscopic beam thickness.

13. The method of claim 2 where an x-ray fanbeam or x-ray slicebeam is discontinuous in the plane of the object, when x-ray transmissive focusing devices, that are either a polymicrocapillary lens or a microchannel plate are used to focus the x-ray beam laterally, in the horizontal direction, to at least seven centimeters long in the object plane, while still maintaining a microscopic beam thickness;

provided that the non-illuminated areas of discontinuity are no more than three percent of the illuminated area in the plane of the object and also that the centers of the equally-spaced microscopic x-ray illuminated areas reside on a single line.

* * * * *

UNITED STATES PATENT AND TRADEMARK OFFICE
CERTIFICATE OF CORRECTION

PATENT NO.    : 6,594,335 B2
DATED         : July 15, 2003
INVENTOR(S)   : Charles J. Davidson It is certified that error appears in the above-identified patent and that said Letters Patent is hereby corrected as shown below:

Delete the title page and insert therefor the attached title page.

Delete Drawing sheets 1 and 2 and insert therefor the attached Drawing Sheets 1 and 2.

<u>Title page,</u>
Item [56], References Cited, U.S. PATENT DOCUMENTS, insert:

-- 5,850,425    12/1998    Wilkins --

Signed and Sealed this

Sixth Day of January, 2004

JAMES E. ROGAN
*Director of the United States Patent and Trademark Office*

(12) United States Patent
Davidson

(10) Patent No.: US 6,594,335 B2
(45) Date of Patent: Jul. 15, 2003

(54) X-RAY PHASE-CONTRAST MEDICAL MICRO-IMAGING METHODS

(76) Inventor: Charles J. Davidson, 1337 W. Farnum Ave., Royal Oak, MI (US) 48067

(*) Notice: Subject to any disclaimer, the term of this patent is extended or adjusted under 35 U.S.C. 154(b) by 0 days.

(21) Appl. No.: 09/749,978

(22) Filed: Dec. 27, 2000

(65) Prior Publication Data
US 2001/0038680 A1 Nov. 8, 2001

Related U.S. Application Data
(60) Provisional application No. 60/173,238, filed on Dec. 28, 1999.

(51) Int. Cl.⁷ .................................................. G21K 7/00
(52) U.S. Cl. ........................ 378/43; 378/119; 378/143
(58) Field of Search ............................ 378/43, 119, 143

(56) References Cited
U.S. PATENT DOCUMENTS 4,979,203 A * 12/1990 Radocaj ..................... 378/206
5,550,887 A * 8/1996 Schmal et al. ............... 378/43
5,606,588 A * 2/1997 Umstadter et al. .......... 378/119

* cited by examiner

Primary Examiner—Drew A. Dunn
Assistant Examiner—Jurie Yun

(57) ABSTRACT

These methods describe a collimated x-ray beam, used for in vivo phase-contrast x-ray imaging of the interior architecture of carbon-based objects, such as the intact human soft-tissue anatomy, for mapping the decrements of refraction experienced by the incident x-ray beam. These methods utilize a microscopically-thin laser-produced plasma x-ray spatial line-source, specified in the target plane as 50 microns or less in width and orthogonally, greater than one centimeter in length, requiring an optically-reflective mirror to line-focus cylindrically-shaped femptosecond pulses of infrared laser photons onto a heavy metal target. Bragg-diffractive multilayer x-ray mirrors collect a wide solid-angle of characteristic hard x-rays in the 15 KeV-to-100 KeV range from the spatial line-source, yielding a microscopically-thin x-ray fanbeam or x-ray slicebeam, specified in the object plane as 50 microns or less in width and orthogonally, greater than seven centimeters in length. These methods may employ slot-scanning and computed tomography for microscopic clinical x-ray imaging, such as for cancer-detection.

13 Claims, 2 Drawing Sheets